(12) United States Patent
Rittsteiger et al.

(10) Patent No.: US 10,519,096 B2
(45) Date of Patent: Dec. 31, 2019

(54) PROCESS FOR PREPARING AMINO COMPOUNDS FROM NITRILE COMPOUNDS

(71) Applicant: Evonik Degussa GmbH, Essen (DE)

(72) Inventors: Anne Rittsteiger, Meltingen (CH); Stephan Kohlstruk, Gladbeck (DE); Dirk Hoppe, Nottuln (DE); Alexander Martin Rüfer, Recklinghausen (DE); Sabrina Sowka, Dülmen (DE); Sven Schneider, Datteln (DE); Norbert Schlüter, Gescher (DE); Axel Hengstermann, Senden (DE); Markus Galle, Dortmund (DE); Stefan Röder, Sinntal (DE); Monika Berweiler, Maintal (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/982,590

(22) Filed: May 17, 2018

(65) Prior Publication Data

US 2018/0339959 A1    Nov. 29, 2018

(30) Foreign Application Priority Data

May 23, 2017  (EP) .................................. 17172376

(51) Int. Cl.
| | | |
|---|---|---|
| *C07C 209/52* | (2006.01) | |
| *C07C 209/48* | (2006.01) | |
| *C07C 209/26* | (2006.01) | |
| *C07C 211/36* | (2006.01) | |

(52) U.S. Cl.
CPC .......... *C07C 209/52* (2013.01); *C07C 209/26* (2013.01); *C07C 209/48* (2013.01); *C07C 211/36* (2013.01); *C07C 2521/02* (2013.01); *C07C 2523/86* (2013.01); *C07C 2601/14* (2017.05)

(58) Field of Classification Search
None
See application file for complete search history.

(56) References Cited

U.S. PATENT DOCUMENTS

| | | |
|---|---|---|
| 3,352,913 A | 11/1967 | Schmitt et al. |
| 4,429,157 A | 1/1984 | Disteldorf et al. |
| 5,371,292 A | 12/1994 | Merger et al. |
| 5,491,264 A | 2/1996 | Herkes et al. |
| 5,589,596 A | 12/1996 | Furutani et al. |
| 5,679,860 A | 10/1997 | Haas et al. |
| 5,852,217 A | 12/1998 | Haas et al. |
| 6,011,179 A | 1/2000 | Haas et al. |
| 6,437,186 B1 | 8/2002 | Ostgard et al. |
| 6,649,799 B2 | 11/2003 | Ostgard et al. |
| 9,085,506 B2 | 7/2015 | Galle et al. |
| 9,862,673 B2 | 1/2018 | Rufer et al. |
| 9,937,483 B2 | 4/2018 | Kohlstruk et al. |
| 2010/0094058 A1* | 4/2010 | Lettmann ................ B01J 25/00 564/492 |
| 2011/0218362 A1 | 9/2011 | Ostgard et al. |
| 2013/0261341 A1 | 10/2013 | Lettmann et al. |
| 2017/0275232 A1 | 9/2017 | Wigbers et al. |
| 2017/0226044 A1 | 10/2017 | Rittsteiger et al. |
| 2017/0355662 A1 | 12/2017 | Rufer et al. |
| 2017/0362163 A1 | 12/2017 | Kohlstruk et al. |

FOREIGN PATENT DOCUMENTS

| | | | |
|---|---|---|---|
| CA | 2015251 A1 | 10/1990 | |
| CN | 104230721 B | 5/2013 | |
| DE | 4426472 A1 | 2/1995 | |
| DE | 19627265 A1 | 1/1998 | |
| EP | 42119 B1 | 12/1981 | |
| EP | 0394967 A1 | 10/1990 | |
| EP | 0394967 A1 * | 10/1990 | ........... C07C 209/48 |
| EP | 449089 B1 | 3/1991 | |
| EP | 623585 A1 | 9/1994 | |
| EP | 816323 A2 | 7/1998 | |
| EP | 913387 B1 | 6/1999 | |
| WO | 2012076315 A1 | 6/2012 | |
| WO | 2012126869 A1 | 9/2012 | |
| WO | 2012126956 A1 | 9/2012 | |
| WO | 2016030383 A1 | 3/2016 | |

OTHER PUBLICATIONS

Eigenberger, Review of Fixed-Bed Reactors, Ullmann's Encyclopedia of Industrial Chemistry. vol. B4, 1992, VCH Publishers. Inc, pp. 199-238. (Year: 1992).*
Eigenberger, Review of Fixed-Bed Reactors, Ullmann's Encyclopedia of Industrial Chem. vol. B4, 1992, VCH Publ. Inc, pp. 199-238. (Year: 1992).*

* cited by examiner

*Primary Examiner* — Clinton A Brooks
*Assistant Examiner* — Kofi Adzamli
(74) *Attorney, Agent, or Firm* — Philip P. McCann; Nexsen Pruet PLLC

(57) ABSTRACT

The present invention relates to a process for hydrogenating nitrile compounds to amino compounds, in which the cross-sectional loading of the reactor during the hydrogenation is less than or equal to 4.0 kg/m$^2$*s, based on the liquid phase.

20 Claims, No Drawings

PROCESS FOR PREPARING AMINO COMPOUNDS FROM NITRILE COMPOUNDS

CROSS REFERENCE TO RELATED APPLICATIONS

This application is a 35 U.S.C. § 111(c) U.S. national phase entry of European Patent Office Application No. 17172376.0 having a filing date of May 23, 2017, of which is incorporated herein by reference in its entirety.

FIELD

The invention relates to an improved process for preparing amino compounds from nitrile compounds. Nitrile groups can be converted via hydrogenation into aminomethyl groups. Optionally, other reducible functional groups, such as imino groups for example, can likewise be hydrogenated. In the presence of ammonia, ketonitriles in particular can also be converted into amino compounds (having at least two amino groups) via aminating hydrogenation (single- or multi-stage conversion of oxo groups into amino groups in the presence of ammonia and also reduction of the nitrile groups to aminomethyl groups). The present invention relates more particularly to an improved process for the aminating hydrogenation of 3-cyano-3,5,5-trimethylcyclohexanone, also known as isophoronenitrile or abbreviated to IPN, to give 3-aminomethyl-3,5,5-trimethylcyclohexylamine, also known as isophoronediamine or abbreviated to IPDA.

BACKGROUND

The preparation of IPDA by aminating hydrogenation of IPN is known and has already been described many times.

In the simplest case (U.S. Pat. No. 3,352,913 A), IPN is reacted in the presence of hydrogen and of an excess of ammonia over a cobalt catalyst. IPN and ammonia initially react with elimination of water to form isophoronenitrile imine, IPNI, which is subsequently hydrogenated to IPDA.

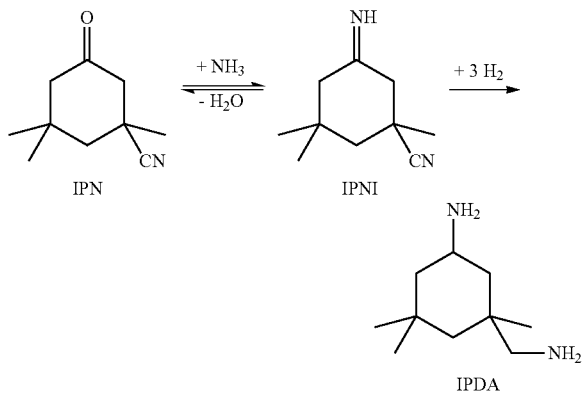

When the reaction is conducted in this way, the yield of IPDA is determined to a crucial degree by the excess of ammonia. The maximum IPDA yields achieved are about 80%. The main by-product is what is called the amino alcohol, IPAA, which results from the direct hydrogenation of the IPN.

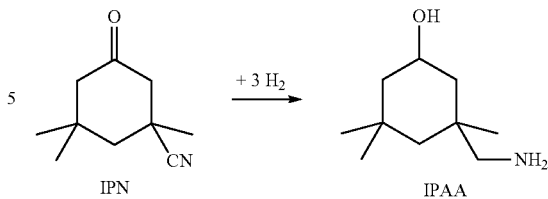

A significant rise in the IPDA yield is achieved when the formation of IPNI is accelerated by use of suitable imination catalysts. Suitable imination catalysts are, for example, acidic ion exchange resins (EP 0 042 119 B1). In addition, it is also possible to use acidic metal oxides (EP 0 449 089 B1), sulphonic acid group-containing organopolysiloxanes (EP 0 816 323 A1), heteropolyacids (DE 44 26 472 A1) and activated carbon (EP 0 623 585 A1) as imination catalysts. As well as the reduction of the unwanted amino alcohol, other by-products are also distinctly suppressed, for example bicyclic compounds and those by-products which result from the elimination of HCN.

DETAILED DESCRIPTION

Particular reference is made to the problem of elimination of HCN from gamma-ketonitriles, such as IPN, in the literature (U.S. Pat. No. 3,352,913 A). Firstly, it is noted that HCN elimination reduces the yield of IPDA (EP 0 042 119 B1, DE 44 26 472 A1). Secondly, it is pointed out that HCN acts as a catalyst poison and leads to deactivation of the hydrogenation catalyst (EP 0 394 967 A1, page 2 line 34 ff, page 3 line 44 ff). It is therefore advisable to conduct the imination step in such a way that a minimum amount of HCN is eliminated.

According to EP 0 913 387 B1, selectivity can also be enhanced in the preparation of IPDA by using quaternary ammonium bases. Correspondingly modified catalysts, specifically in the case of use of a solvent, have a much longer service life than alkali-modified catalysts.

According to WO 2012/126956 A1, the hydrogenation of nitriles is carried out preferably at a cross-sectional loading of the liquid reaction phase in the range of 5 to 50 kg/m$^2$*s. These high cross-sectional loadings are generally achieved by relatively high circulation streams (return stream) with respect to the feedstock stream supplied (forerun). For instance, particular ratios of circulation stream to feedstock stream supplied are set from 0.5:1 to 250:1, and especially preferably from 2:1 to 180:1. The reaction regime therefore corresponds to a continuous circuit. A disadvantage in this case is that a corresponding process regime requires a complex reaction set-up and a trickle bed mode of the liquid and gaseous reactants over the solid catalyst bed cannot be carried out, due to the high circulation streams, to achieve a high degree of conversion.

In addition, processes for producing isophoronediamine are known from CN 104230721 B, WO 2012/076315 A1 and WO 2012/126869 A1.

SUMMARY

With respect to the prior art, the object is therefore to provide a process for hydrogenating nitrile compounds to amino compounds which avoids the disadvantages of the prior art. In particular, the object is to provide a process for hydrogenating nitriles to amino compounds which is technically less complex and which affords the desired amino compounds with high yields and selectivities.

It has been found that, surprisingly, the present object is achieved by the process according to the invention for hydrogenating nitrile compounds to amino compounds, in which the cross-sectional loading of the reactor during the hydrogenation is less than or equal to 4.0 kg/m²*s, based on the liquid phase.

Nitrile compounds are understood here and in the following to mean organic compounds comprising nitrile groups (and optionally further functional groups such as, for example, oxo, imino or amino groups). The nitrile compounds to be used can be in particular aliphatic, cycloaliphatic or aromatic mono-, di- or polynitrile compounds. Aliphatic compounds may be linear or branched. Cycloaliphatic compounds have cyclic and optionally linear and/or branched portions. Correspondingly, aromatic compounds have aromatic and optionally linear and/or branched portions.

It is possible to use, preferably, aliphatic mono-, di- and/or trinitriles having 1 to 30, in particular 2 to 18, especially preferably 2 to 9 carbon atoms, cycloaliphatic mono- and dinitriles having 6 to 20, in particular 6 to 13 carbon atoms, or linear, branched or cyclic alpha-, beta-, gamma- or omega-aminonitriles, -iminonitriles or -ketonitriles having 1 to 30, particularly 2 to 13 carbon atoms.

It is also possible to use, preferably, aromatic nitriles having 6 to 18 carbon atoms.

The mono-, di- or trinitriles mentioned above may additionally preferably be mono- or polysubstituted.

Particularly preferred mononitrile compounds are acetonitrile for preparing ethylamines, propionitrile for preparing propylamines, butyronitrile for preparing butylamines, lauronitrile for preparing laurylamine, stearylnitrile for preparing stearylamine, N,N-dimethylaminopropionitrile (DMAPN) for preparing N,N-dimethylaminopropylamine (DMAPA) and benzonitrile for preparing benzylamine.

Particularly preferred dinitrile compounds are adipodinitrile (ADN) for preparing hexamethylenediamine (HMD) and/or 6-aminocapronitrile (ACN), a mixture, especially a mixture in the ratio from 50:50 to 70:30, of 2,4,4-trimethylhexamethylenedinitrile and 2,2,4-trimethylhexamethylenedinitrile (TMN) for preparing an isomeric mixture consisting of 2,4,4-trimethylhexamethylenediamine and 2,2,4-trimethylhexamethylenediamine (TMD), 2-methylglutarodinitrile for preparing 2-methylglutarodiamine, succinonitrile for preparing 1,4-butanediamine and suberic acid dinitrile for preparing octamethylenediamine.

Particularly preferred cyclic nitriles are isophoronenitrile imine (IPNI) and/or isophoronenitrile (IPN) for preparing isophoronediamine and isophthalodinitrile for preparing meta-xylylenediamine.

Particularly preferred β-aminonitriles are aminopropionitrile for preparing 1,3-diaminopropane or addition products of alkylamines, alkyldiamines or alkanolamines of acrylonitrile. For instance, addition products of ethylenediamine and acrylonitrile are reacted to the corresponding diamines. For example, 3-[2-aminoethyl]amino]propionitrile can be converted to 3-(2-aminoethyl)aminopropylamine and 3,3'-(ethylenediimino)bispropionitrile or 3-[2-(3-aminopropylamino)ethylamino]propionitrile can be converted to N,N'-bis(3-aminopropyl)ethylenediamine.

Particularly preferred ω-aminonitriles are aminocapronitrile for preparing hexamethylenediamine.

Further particularly preferred α-nitriles, so-called "Strecker nitriles", are iminodiacetonitrile (IDAN) for preparing diethylenetriamine and aminoacetonitrile (AAN) for preparing ethylenediamine (EDA) and diethylenetriamine (DETA).

A preferred trinitrile is trisacetonitrilamine.

With very particular preference, the process according to the invention is suitable for hydrogenating a mixture, especially a mixture in the ratio from 50:50 to 70:30, of 2,4,4-trimethylhexamethylenedinitrile and 2,2,4-trimethylhexamethylenedinitrile (TMN) to an isomeric mixture consisting of 2,4,4-trimethylhexamethylenediamine and 2,2,4-trimethylhexamethylenediamine (TMD) or for hydrogenating isophoronenitrile or isophoronenitrile imine to isophoronediamine.

Very particularly suitable, since a particularly simple reactor set-up can be implemented, is the process according to the invention for the aminating hydrogenation of isophoronenitrile to isophoronediamine, suitable that is for reacting isophoronenitrile with ammonia and simultaneous or subsequent hydrogenation to isophoronediamine.

This especially preferred process is preferably carried out in this case such that A) isophoronenitrile is subjected directly in one stage to aminating hydrogenation to give isophoronediamine in the presence of ammonia, hydrogen, a catalyst and possibly further additions, and in the presence or absence of organic solvents;

or

B) isophoronenitrile is reacted in at least two stages, wherein said isophoronenitrile is initially converted in a first stage entirely or partly to isophoronenitrile imine which, as a pure substance or in a mixture with other components and possibly unreacted isophoronenitrile, is hydrogenated in at least one subsequent stage to give isophoronediamine in the presence of at least ammonia, hydrogen and a catalyst.

Surprisingly, it has been found that cross-sectional loadings of the reactor during the hydrogenation of less than or equal to 4 kg/m²*s achieve the objects according to the invention. The figures for the cross-sectional loading therefore refer, particularly in the case of a multi-stage aminating hydrogenation, only to the step(s) in which hydrogen is used as reactant.

The cross-sectional loading of the reactor is calculated by means of formula (1) with the cross section A of the reactor (unit [m²]) and the mass flow rate ṁ (unit: [kg/s]) of liquid or dissolved reactants, ammonia and optionally solvents and/or further liquid reaction components (e.g. refluxes). The gas phase of the reaction (e.g. hydrogen, inert gases) is not taken into account when calculating the cross-sectional loading.

$$\text{Cross} - \text{sectional loading} = \frac{\dot{m}}{A} \left[ \frac{\text{kg}}{\text{m}^2 * \text{s}} \right] \qquad (1)$$

Particularly good results can be achieved, especially for the synthesis of isophoronediamine from isophoronenitrile or isophoronenitrile imine and for the synthesis of TMD from 2,4,4-trimethylhexamethylenedinitrile and 2,2,4-trimethylhexamethylenedinitrile, if the cross-sectional loading is 0.01 to 4.0 kg/m²*s, more preferably 0.05 to 3.0 kg/m²*s and especially preferably 0.05 to 2.0 kg/m²*s.

The process according to the invention is preferably carried out in a tubular reactor. Preference is given to a fixed-bed reactor. The reactor is especially preferably a trickle bed reactor.

The reactor is operated in accordance with the invention in a continuous mode, i.e. the process according to the invention is a continuous process. The liquid or dissolved reactants, ammonia optionally required and optionally solvent and/or further liquid components flow through the reactor only once without direct recycling of liquid reaction constituents. However, it is possible that incompletely reacted constituents of the reaction, optionally after removal of ammonia and/or solvent present, are supplied to the feedstock stream prior to inlet into the reactor.

Particularly preferably, especially in the hydrogenation of isophoronenitrile or isophoronenitrile imine, the ratio of circulation stream to the feedstock stream supplied is in the range from 0:1 to 0.49:1, more preferably in the range from 0:1 to 0.25:1, especially preferably in the range from 0:1 to 0.1:1.

The hydrogenation, especially the aminating hydrogenation of isophoronenitrile or isophoronenitrile imine, is preferably conducted at temperatures between 20 and 150° C., particularly preferably 40 and 130° C., and pressures of 0.3 to 50 MPa, preferably 5 to 30 MPa.

The hydrogenation can be conducted in the presence or absence of a solvent. The hydrogenation is preferably conducted in the presence of a solvent. The solvent used can be a solvent known to those skilled in the art and that can be used under the conditions mentioned above. The hydrogenation is preferably carried out in organic solvents and/or liquid ammonia.

A preferred embodiment of the process according to the invention is a process for preparing isophoronediamine in a two-stage or multi-stage process: In the first stage, at least some of the IPN used, in the presence or absence of an imination catalyst and/or of solvent, is converted by reaction with ammonia to isophoronenitrile imine. The conversion of IPN to IPNI after the imination is preferably greater than 80%, particularly preferably greater than 90%, especially preferably greater than 95%.

In at least one further stage, preferably in a second stage, the first stage reaction product, as obtained or after a further treatment and/or addition of further ammonia, is hydrogenated in the presence of at least one hydrogenation catalyst in the presence of ammonia and hydrogen and in the presence or absence of an organic solvent at a temperature of 20 to 150° C., preferably 40 to 130° C., and a pressure of 0.3 to 50 MPa, preferably 5 to 30 MPa.

In a further preferred embodiment, the conversion of IPN to IPDA is effected in three separate reaction spaces. In the first reaction space, IPN is converted to isophoronenitrile imine with excess ammonia over imination catalysts at temperatures between 20 and 150° C. and pressures between 5 and 30 MPa. In the second reaction space, the reaction products formed are hydrogenated with hydrogen in the presence of excess ammonia over hydrogenation catalysts at temperatures between 20 and 130° C. and pressures of 5 to 30 MPa. In the third reaction space, the reaction products formed are hydrogenated over the catalysts for use in accordance with the invention at temperatures between 100 and 160° C. and pressures of 5 to 30 MPa.

In order to accelerate the establishment of equilibrium in the imination reaction, it is preferable to use an imination catalyst. For this purpose, the imination catalysts known according to the prior art can be used. Suitable catalysts are, for example, inorganic or organic ion exchangers (see EP 0 042 119 B1), supported heteropolyacids (see DE 44 26 472 A1), acidic metal oxides, especially aluminium oxide and titanium dioxide (see EP 0 449 089 B1), organopolysiloxanes containing sulfonic acid groups (DE 19627265.3), and acidic zeolites and activated carbon (EP 0 623 585 A1). In the case of use of an imination catalyst, the reaction temperature is between 10 and 150° C., preferably between 30 and 130° C. and especially preferably between 40 and 100° C. The pressure is between the intrinsic pressure of the mixture and 50 MPa. Preference is given to conducting the imination reaction at the pressure at which the subsequent hydrogenation is also conducted.

Even though the imination of isophoronenitrile with liquid ammonia is preferably conducted without addition of further solvents, it can also work in the presence of additional solvents. Suitable solvents are monohydric alcohols having 1 to 4 carbon atoms, especially methanol, and ethers, particularly THF, MTBE and dioxane.

In the imination stage, between 1 and 500 mol, preferably 5 and 200 mol, more preferably between 5 and 100 mol, of ammonia are used per mole of IPN used. Typical catalyst hourly space velocities are in the range from 0.01 to 10 kg of IPN per kg of catalyst and hour, preferably 0.5 to 10 and more preferably 0.5 to 5 kg of IPN per kg of catalyst and hour.

In the case of imination in the presence of an imination catalyst, the catalyst may be present in the form of a suspension catalyst or fixed bed catalyst. It is advantageous to use fixed bed catalysts. In a particularly preferred embodiment, IPN and ammonia are passed continuously from the bottom upwards through a reaction tube filled with imination catalyst.

The hydrogenation, especially the hydrogenation of isophoronenitrile or isophoronenitrile imine or of 2,4,4-trimethylhexamethylenedinitrile and 2,2,4-trimethylhexamethylenedinitrile, is preferably conducted at temperatures between 20 and 150° C., particularly preferably 40 and 130° C., and pressures of 0.3 to 50 MPa, preferably 5 to 30 MPa. It is also possible to carry out the hydrogenation in the presence of solvents, especially in the presence of a solvent present in a preceding imination stage. The main advantage in the case of use of a solvent is that the hydrogenation can be conducted at lower pressures between 0.3 and 10 MPa.

The hydrogen required for the hydrogenation may be supplied to the reactor either in excess, for example at up to 10 000 molar equivalents, or merely in an amount such that the hydrogen consumed by reaction, and the portion of the hydrogen that leaves the reactor dissolved in the product stream, is replenished. In the case of a continuous mode of operation, the hydrogen may be supplied in cocurrent or countercurrent flow.

In a preferred embodiment, the hydrogenation is effected in liquid ammonia as solvent. Between 1 and 500 mol, preferably 5 and 200 mol, especially preferably between 5 and 100 mol of ammonia are used per mole of nitrile compound to be hydrogenated, preferably per mole of isophoronenitrile, isophoronenitrile imine, 2,4,4-trimethylhexamethylenedinitrile or 2,2,4-trimethylhexamethylenedinitrile. In the case of an upstream imination, the amount of ammonia that can be used advantageously in the hydrogenation has been adjusted in the preceding stage. However, the ammonia content can also be increased to the desired value before the hydrogenation by addition of additional ammonia.

The catalysts used for the hydrogenation may in principle be any catalysts which catalyze the hydrogenation of nitrile and/or imine groups with hydrogen. A fixed-bed catalyst is preferably used as catalyst. The fixed-bed catalyst in the process according to the invention is especially preferably used in trickle bed mode.

Particularly suitable catalysts are nickel, copper, iron, palladium, rhodium, ruthenium and cobalt catalysts, very particularly ruthenium and cobalt catalysts. To increase activity, selectivity and/or service life, the catalysts may additionally comprise doping metals or other modifiers. Typical doping metals are, for example, Mo, Fe, Ag, Cr, Ni, V, Ga, In, Bi, Ti, Zr and Mn, and the rare earths. Typical modifiers are, for example, those with which the acid-base properties of the catalysts can be influenced, preferably alkali metals and alkaline earth metals or compounds thereof, preferably magnesium and calcium compounds, and also phosphoric acid or sulphuric acid and compounds thereof.

The catalysts may be employed in the form of powders or shaped bodies, for example extrudates or compressed powders. It is possible to employ unsupported catalysts, Raney-type catalysts or supported catalysts. Preference is given to Raney-type and supported catalysts. Suitable support materials are, for example, silicon dioxide, aluminium oxide, aluminosilicates, titanium dioxide, zirconium dioxide, kieselguhr, aluminium-silicon mixed oxides, magnesium oxide and activated carbon. The active metal can be applied to the support material in a manner known to those skilled in the art, for example by impregnation, spray application or precipitation. Depending on the method of catalyst production, further preparation steps known to those skilled in the art are necessary, for example drying, calcining, shaping and activation. Further assistants, for example graphite or magnesium stearate, may optionally be added for shaping.

It is preferable that the hydrogenation catalysts for use are first conditioned with ammonia before they are used in the hydrogenation. To this end, the catalysts are contacted with ammonia or with mixtures of ammonia and one or more solvents. The conditioning preferably follows installation of the catalysts in the hydrogenation reactor, but it can also precede the installation of the catalysts. For conditioning, between 0.2 and 3, preferably 0.5 and 2 m$^3$ of ammonia per m$^3$ of catalyst and hour are used. It is customary to work at temperatures between 20 and 150° C., preferably 40 to 130° C. Particular preference is given to running through a temperature ramp in which the catalyst, beginning at moderately elevated temperature, preferably between 20 and 50° C., is heated gradually up to the reaction temperature desired at a later stage for the hydrogenation, preferably 20 to 150° C. The conditioning is preferably conducted in the presence of hydrogen, the partial pressure of the hydrogen used in the reactor covering the range from 0.1 to 50 MPa, preferably 5 to 40 MPa, more preferably 10 to 30 MPa. The duration of the conditioning, depending on the amount of ammonia used, is preferably between 1 and 48 h, more preferably between 12 and 24 h.

A Raney-type catalyst is preferably used for the hydrogenation. A particularly preferred catalyst after activation in its entirety has the following composition in weight percent (wt %), wherein the proportions add up to 100 wt %, based on the metals present:
cobalt: 55 to 95 wt %
aluminium: 5 to 45 wt %
chromium: 0 to 3 wt %
nickel: 0 to 7 wt %

This preferred catalyst is present preferably in the form of irregular particles as granules and after activation has particle sizes of 1 to 8 millimetres (mm).

The preferred catalyst consists of a metal alloy, the metal alloy having been surface activated by bases. The layer thickness of the activated layer on the particle surface of the catalyst is preferably 50 to 1,000 micrometres (µm). However, it may also be greater or smaller. Accordingly, the catalytically active composition of the catalyst is located on the surface. Alternatively, it is possible in the context of the invention to almost entirely or entirely leach out the entire catalyst particle.

The particle sizes reported may also have a statistical size distribution within the range. Both narrow distributions and broad distributions are in accordance with the invention.

The determination of the particle sizes is described in DIN ISO 9276-1 (September 2004) and 9276-2 (February 2006) and 9276-4 (February 2006) and 9276-6 (January 2012). In addition, exact particulars concerning the definition of particle sizes, the distribution of particle sizes and the measurement of particle sizes may be found in HORIBA® Scientific, A GUIDEBOOK TO PARTICLE SIZE ANALYSIS, 2012, from HORIBA® Instruments, Inc, Irvine, USA.

According to the invention, the distribution of the particle sizes and the measurement of the particle sizes can be determined by laser methods (ISO 13320, 2012), light methods or imaging methods.

The inventive catalyst is preferably obtained by sieving the granules produced. This produces what are called sieve fractions. This may involve mixing individual sieve fractions, or a catalyst is obtained by single or multiple sieving. The catalysts thus produced have a statistical distribution of particle sizes, typically in the form of a Gaussian distribution. Symmetric and also asymmetric distributions are possible.

Suitable methods and descriptions of sieve analysis are given in:
DIN 66165-1:1987-04 Particle size analysis; sieve analysis; general principles, and in DIN 66165-2:1987-04 Particle size analysis; sieve analysis; procedure.
Paul Schmidt, Rolf Körber, Matthias Coppers: *Sieben und Siebmaschinen* (*Sieving and sieving machines*): *Grundlagen und Anwendung* (*Fundamentals and Applications*). Wiley-VCH Verlag, 2003, ISBN 9783527302079, chapter 4.4: Analysesiebung (sieve analysis). Jörg Hoffmann: *Handbuch der Messtechnik* (*Handbook of measurement techniques*). Hanser Verlag, 2007, ISBN 978-3-446-40750-3, chapter 3.12.16.2.1.

General methods for preparing the catalyst for the hydrogenation:

a) Production of the Alloy

The alloy is produced by thermal means, for example in an induction oven. This involves melting the metals to obtain an alloy. For further processing the finished melt is cast into bars for example.

b) Production of the Granules

The alloy is processed to afford granules in suitable equipment, for example precomminuted by means of a jaw crusher and subjected to further grinding by means of a roll mill. A sieving step gives the desired size distribution of the granules through choice of appropriate sieves (e.g. 3-7 mm).

c) Activation of the Catalyst

The catalyst is activated in suitable apparatus. Organic or inorganic bases may be employed. Preference is given to using a lye (e.g. sodium hydroxide solution) where, by an exothermic process, a portion of the aluminium is leached out of the alloy to form hydrogen and aluminate liquor. The concentration of the lye may be between 5 and 30 wt % and the reaction temperature between 50° C. and 100° C. The degree of activation is determined by the temperature and the reaction time. The reaction time is variable and depends on the reaction conditions and the desired degree of activation. After activation, the catalyst is washed with water and then stored under water.

Other compositions may be produced analogously in production step a) through appropriate choice of metal amounts.

The catalyst is preferably produced in the sequence described. However, the catalyst may also be activated prior to the production of the granulates.

To increase activity, selectivity and/or service life, the catalysts may additionally comprise doping metals or other modifiers. Typical doping metals are for example Mo, Fe, Ag, V, Ga, In, Bi, Ti, Zr and Mn and also the rare earths alone or in mixtures. Typical modifiers are, for example, those with which the acid-base properties of the catalysts can be influenced, preferably alkali metals and alkaline earth metals or compounds thereof, preferably magnesium and lithium compounds. If such compounds are present, in an amount of not more than 5 wt %, there is a corresponding reduction in the proportion of the abovementioned metals Co and Al and, if present, Cr and Ni in the catalyst, the proportions of Co and Al and, if present, Cr and Ni after activation adding up to at least 95 wt %, based on the metals present.

EXAMPLES

Production of the Catalyst, Cobalt Granules:
a) Production of the Alloy

The alloy is produced in an induction oven. This involves melting the metals in the appropriate amounts at 1500° C. The finished melt is cast to bars for further processing.

b) Production of the Granules

The alloy bars are precomminuted by means of a jaw crusher and ground further by means of a roll mill. A sieving step gives the desired size distribution of the granules through the choice of the appropriate sieves.

c) Activation of the Catalyst

The catalyst can be activated in a standard glass laboratory apparatus, for example in a glass beaker. An aqueous lye (e.g. sodium hydroxide solution) was added to the granules with stirring. The granules are in a catalyst basket during the activation. An exothermic operation leaches a portion of the aluminium out of the alloy with formation of hydrogen and sodium aluminate solution. The employed lye had a concentration of 20 wt % and the reaction temperature was 90° C. The degree of activation was determined via the reaction time. After activation, the catalyst is washed with water and then stored under water.

After activation the employed catalyst in its entirety has the following composition in weight percent (wt %), wherein the proportions add up to 100 wt %, based on the metals present:
cobalt: 55% by weight
aluminium: 42% by weight
chromium: 1% by weight
nickel: 2% by weight A sieve fraction was used with particle sizes of the catalyst, i.e. the granule particles, having a statistical distribution between 2.0 and 5.0 millimetres (mm), where up to 10 percent of the particles may also be outside said range of said lower limit or upper limit, but up to 10 percent in each case may also be outside said range of said lower limit and upper limit.

Preparation of IPDA

Catalysts are tested for their catalytic activity in the preparation of 3-aminomethyl-3,5,5-trimethylcyclohexylamine (isophoronediamine, IPDA) from 3-cyano-3,5,5-trimethylcyclohexanone (isophoronenitrile, IPN) in a two-stage process.

In the first reaction stage, isophoronenitrile was at least partly converted to 3-cyano-3,5,5-trimethylcyclohexane imine with ammonia in the presence of an imination catalyst at 45° C. and, in the second reaction stage, subjected to aminating hydrogenation with hydrogen in the presence of ammonia over a hydrogenation catalyst at a temperature of 100° C. and a pressure of 250 bar. Each stage of the preparation was conducted in a separate reactor with individual temperature control. Both reactors, however, were connected in series in this case.

The hydrogenation reactor used has an internal diameter of 2 cm and was filled with 37 ml of the catalyst to be tested. The input solution of IPN (14.6 wt %) and ammonia (85.4 wt %) was pumped through the reaction tube from the top downwards at a volume flow rate of 108 ml/h, which corresponds to a cross-sectional loading of 0.06 kg/m$^2$*s. The hydrogen was added separately, likewise from the top, at a volume flow rate of 40 Nl/h. The product solution was collected beneath the reactor in a separating vessel and the composition thereof investigated by gas chromatography. The result is reported in Table 1.

TABLE 1

| Temperature | Cross-sectional loading | IPDA yield/GC % | Conversion |
| --- | --- | --- | --- |
| 100° C. | 0.06 kg/m$^2$ * s | 96.9% | 99.9% |

Preparation of TMD

Catalysts for the preparation of trimethylhexamethylenediamine (TMD) from trimethylhexamethylenedinitrile (TMN) are tested for their catalytic activity in a single-stage continuous process.

In the reaction, TMN was hydrogenated with hydrogen over a hydrogenation catalyst (cobalt granules) at a temperature of 80° C. and a pressure of 250 bar in the presence of ammonia as solvent.

The hydrogenation reactor used has an internal diameter of 2 cm and was filled with 42 ml of the catalyst to be tested. The input solution of TMN (14.6 wt %) and ammonia (85.4 wt %) was pumped through the reaction tube from the top downwards at a volume flow rate of 120 ml/h, which corresponds to a cross-sectional loading of 0.08 kg/m$^2$*s. The hydrogen was added separately, likewise from the top, at a volume flow rate of 40 Nl/h. The product solution was collected beneath the reactor in a separating vessel and the composition thereof investigated by gas chromatography. The result is reported in Table 2.

TABLE 2

| Temperature | Cross-sectional loading | Yield of TMD/GC % | Conversion |
| --- | --- | --- | --- |
| 80° C. | 0.08 kg/m$^2$ * s | 91.3% | 99.9% |

The invention claimed is:

1. A process for hydrogenating nitrile compounds to amino compounds, wherein the process is selected from the group consisting of
   (a) hydrogenating a mixture in the ratio of from 50:50 to 70:30 of 2,4,4-trimethylhexamethylenedinitrile and 2,2,4-trimethylhexamethylenedinitrile to form a mixture consisting of 2,4,4-trimethylhexamethylenediamine and 2,2,4-trimethylhexamethylenediamine;
   (b) hydrogenating an isophoronenitrile to an isophoronediamine; and (c) hydrogenating an isophoronenitrile imine to an isophoronediamine,
wherein the cross-sectional loading of a tubular reactor during the hydrogenation is from 0.01 kg/m$^2$*s to 4.0 kg/m$^2$*s, based on the liquid phase.

2. The process according to claim 1, wherein the nitrile compound is a mixture of 2,4,4-trimethylhexamethylenedinitrile and 2,2,4-trimethylhexamethylenedinitrile in the ratio of from 50:50 to 70:30 wherein the cross-sectional loading of the tubular reactor during the hydrogenation is from 0.05 kg/m$^2$*s to 2.0 kg/m$^2$*s, based on the liquid phase, wherein the tubular reactor is a fixed-bed reactor.

3. The process according to claim 1, wherein isophoronenitrile is subjected to aminating hydrogenation to give isophoronediamine, wherein the tubular reactor is a trickle bed reactor.

4. The process according to claim 3, wherein
A) isophoronenitrile is subjected directly in one stage to aminating hydrogenation to give isophoronediamine in the presence of ammonia, hydrogen, a catalyst and possibly further additions, and in the presence or absence of organic solvents;
or
B) isophoronenitrile is reacted in at least two stages, wherein said isophoronenitrile in initially converted in a first stage entirely or partly to isophoronenitrile imine which, as a pure substance or in a mixture with other components and possibly unreacted isophoronenitrile, is hydrogenated in at least one subsequent stage to give isophoronediamine in the presence of at least ammonia, hydrogen and a catalyst.

5. The process according to claim 4, wherein the cross-sectional loading is from 0.05 to 3.0 kg/m$^2$*s.

6. The process according to claim 3, wherein the process for preparing isophoronediamine is carried out in two or more stages and in that isophoronenitrile is converted in a first stage to isophoronenitrile imine by reaction with ammonia in the presence or absence of an imination catalyst or solvent.

7. The process according to claim 6, wherein the reaction product of the first stage is hydrogenated in the presence of at least one hydrogenation catalyst in the presence of ammonia and hydrogen and in the presence or absence of an organic solvent at a temperature of from 20 to 150° C. and a pressure of from 0.3 to 50 MPa.

8. The process according to claim 3, wherein isophoronenitrile is subjected directly in one stage to aminating hydrogenation to give isophoronediamine in the presence of ammonia, hydrogen, a catalyst and possibly further additions.

9. The process according claim 8, wherein the ratio of circulation stream to the feedstock stream supplied is in the range from 0:1 to 0.49:1.

10. The process according claim 8, wherein the hydrogenation is carried out at temperatures between 20 and 150° C. and pressures of from 0.3 to 50 MPa.

11. The process according to claim 3, wherein isophoronenitrile is reacted in at least two stages, wherein said isophoronenitrile is initially converted in a first stage entirely or partly to isophoronenitrile imine which, as a pure substance or in a mixture with other components and unreacted isophoronenitrile, is hydrogenated in at least one subsequent stage to give isophoronediamine in the presence of at least ammonia, hydrogen and a catalyst.

12. The process according to claim 1, wherein the ratio of circulation stream to the feedstock stream supplied is in the range from 0:1 to 0.49:1, wherein the tubular reactor is a trickle bed reactor.

13. The process according to claim 1, wherein the hydrogenation is carried out at temperatures between 20 and 150° C. and pressures of from 0.3 to 50 MPa, wherein the tubular reactor is a trickle bed reactor.

14. The process according to claim 1, wherein a catalyst is used for the hydrogenation selected from the group consisting of nickel, copper, iron, palladium, rhodium, ruthenium and cobalt catalysts, wherein the tubular reactor is a trickle bed reactor.

15. The process according to claim 14, wherein the hydrogenation catalyst is selected from the group consisting of Raney-type and supported catalysts.

16. The process according to claim 15, wherein the catalyst after activation has a composition in its entirety, in percent by weight based on all proportions of metals present, of

| | |
|---|---|
| cobalt: | from 55 to 95 wt % |
| aluminium: | from 5 to 45 wt % |
| chromium: | from 0 to 3 wt % |
| nickel: | from 0 to 7 wt %. |

17. The process according to claim 1, wherein the process for hydrogenating nitrile compounds to amino compounds comprises the step of hydrogenating isophoronenitrile or isophoronenitrile imine to isophoronediamine having a ratio of a circulation stream to a feedstock stream supplied is in the range from 0:1 to 0.49:1.

18. The process according to claim 17, wherein the ratio of a circulation stream to a feedstock stream supplied is in the range from 0:1 to 0.25:1.

19. The process according to claim 17, wherein the ratio of a circulation stream to a feedstock stream supplied is in the range from 0:1 to 0.1:1.

20. The process according to claim 1, wherein the cross-sectional loading is from 0.05 kg/m$^2$*s to 3.0 kg/m$^2$*s.

* * * * *